United States Patent
Gallagher et al.

(10) Patent No.: US 11,813,060 B2
(45) Date of Patent: Nov. 14, 2023

(54) SYSTEM AND METHOD FOR BIOMETRIC EVOKED RESPONSE MONITORING AND FEEDBACK

(71) Applicant: Lear Corporation, Southfield, MI (US)

(72) Inventors: David Gallagher, Sterling Heights, MI (US); Francesco Migneco, Saline, MI (US); Arjun Yetukuri, Rochester Hills, MI (US); Marie-Eve Cote, Royal Oak, MI (US)

(73) Assignee: LEAR CORPORATION, Southfield, MI (US)

( * ) Notice: Subject to any disclaimer, the term of this patent is extended or adjusted under 35 U.S.C. 154(b) by 425 days.

(21) Appl. No.: 16/915,360

(22) Filed: Jun. 29, 2020

(65) Prior Publication Data

US 2021/0401340 A1     Dec. 30, 2021

(51) Int. Cl.
| | |
|---|---|
| A61B 5/18 | (2006.01) |
| A61B 5/00 | (2006.01) |
| G08B 21/06 | (2006.01) |
| A61B 5/369 | (2021.01) |
| B60Q 9/00 | (2006.01) |

(52) U.S. Cl.
CPC ............ *A61B 5/18* (2013.01); *A61B 5/369* (2021.01); *A61B 5/742* (2013.01); *A61B 5/7405* (2013.01); *A61B 5/746* (2013.01); *A61B 5/7455* (2013.01); *G08B 21/06* (2013.01); *B60Q 9/00* (2013.01)

(58) Field of Classification Search
CPC ......... A61B 5/18; A61B 5/369; A61B 5/7405; A61B 5/742; A61B 5/7455; A61B 5/746; G08B 21/06; B60Q 9/00
See application file for complete search history.

(56) References Cited

U.S. PATENT DOCUMENTS

| | | | |
|---|---|---|---|
| 9,389,595 B2 | 7/2016 | Caskey et al. | |
| 9,536,411 B2 | 1/2017 | Foley et al. | |
| 9,956,963 B2 | 5/2018 | Vijaya et al. | |
| 10,210,409 B1 | 2/2019 | Migneco et al. | |

(Continued)

FOREIGN PATENT DOCUMENTS

| | | |
|---|---|---|
| CN | 106580349 A | 4/2017 |
| CN | 107233103 A | 10/2017 |

OTHER PUBLICATIONS

Freer Logic, "Body Wave Technology", www.freerlogic.com/body-wave/ viewed on May 17, 2017, 4 pages.

*Primary Examiner* — Nabil H Syed
*Assistant Examiner* — Cal J Eustaquio
(74) *Attorney, Agent, or Firm* — Brooks Kushman P.C.

(57) ABSTRACT

In at least one embodiment, a system for performing biometric evoked response monitoring and feedback for a vehicle is provided. The system includes a plurality of sensors and at least one controller. The plurality of sensors may be positioned about a main cabin of the vehicle and each sensor is configured to provide a first signal indicative of a measured electromagnetic characteristic of an anatomical feature of a driver for the vehicle in response to an alert being issued to the driver. The at least one controller is configured to receive the first signal and to determine a stimulus response and an attentiveness response of the driver based on the measured electromagnetic characteristic of the anatomical feature of the driver.

17 Claims, 3 Drawing Sheets

(56) References Cited

U.S. PATENT DOCUMENTS

| | | | |
|---|---|---|---|
| 10,379,535 B2 | 8/2019 | Migneco et al. | |
| 2004/0209594 A1* | 10/2004 | Naboulsi | B60R 16/023 |
| | | | 455/403 |
| 2010/0069775 A1 | 3/2010 | Milgramm et al. | |
| 2010/0234752 A1 | 9/2010 | Sullivan et al. | |
| 2016/0090097 A1 | 3/2016 | Grube et al. | |
| 2017/0071525 A1* | 3/2017 | Lin | G08B 21/06 |
| 2017/0367635 A1* | 12/2017 | Hur | A61B 5/18 |
| 2020/0037945 A1* | 2/2020 | Yoon | B60W 60/0051 |
| 2020/0062275 A1* | 2/2020 | Higgins | G05D 1/0061 |
| 2021/0290134 A1* | 9/2021 | Talamonti | A61B 5/18 |

\* cited by examiner

SYSTEM AND METHOD FOR BIOMETRIC EVOKED RESPONSE MONITORING AND FEEDBACK

TECHNICAL FIELD

Aspects disclosed herein may generally relate to a system and method for biometric evoked response monitoring and feedback. These aspects and others will be discussed in more detail below.

BACKGROUND

U.S. Pat. No. 10,210,409 to Migneco et al. provides a vehicle seating system that can detect and optionally quantify a drowsiness state and/or and emotional state of a seat occupant in the vehicle. A seat is mounted in a vehicle and houses a wireless electromagnetic sensing system at least partially integrated into the seat. These sensed signals can be used to determine the occupant's state. When the state exceeds a threshold, then wireless stimulation emitters output a stimulation signal to the occupant to alter the emotion state or drowsiness state to move the occupant to below the threshold and to a calm state or an alert state. The system can also use additional physiological sensor to measure at least one of a heart rate, a respiration rate, or both of the occupant to be used with the electromagnetic sensing at the seat.

SUMMARY

In at least one embodiment, a system for performing biometric evoked response monitoring and feedback for a vehicle is provided. The system includes a plurality of sensors and at least one controller. The plurality of sensors may be positioned about a main cabin of the vehicle and each sensor is configured to provide a first signal indicative of a measured electromagnetic characteristic of an anatomical feature of a driver for the vehicle in response to an alert being issued to the driver. The at least one controller is configured to receive the first signal and to determine a stimulus response and an attentiveness response of the driver based on the measured electromagnetic characteristic of the anatomical feature of the driver.

In at least one embodiment, a system for performing biometric evoked response monitoring and feedback for a vehicle is provided. The system includes a plurality of sensors and at least one controller. The plurality of sensors may be positioned about a main cabin of the vehicle and each sensor is configured to provide a first signal indicative of a measured electromagnetic characteristic of an anatomical feature of a driver the vehicle in response to a first alert being issued to the driver. The at least controller is configured to receive the first signal and to determine a stimulus response and an attentiveness response of the driver based on the measured electromagnetic characteristic of the anatomical feature of the driver. The at least controller is configured is further configured to change the first alert to a second alert based on the stimulus response and the attentiveness response.

In at least one embodiment, a system for performing biometric evoked response monitoring and feedback for a vehicle is provided. The system includes a plurality of electroencephalographic (EEG) sensors and at least one controller. The EEG sensors may be for being positioned in a vehicle. Each EEG sensor is configured to provide a first signal indicative of a measured electromagnetic characteristic of an anatomical feature of a driver of the vehicle in response to the vehicle transmitting a first alert to the driver. The at least one controller is configured to receive the first signal and to determine a stimulus response and an attentiveness response of the driver based on the measured electromagnetic characteristic of the anatomical feature of the driver. The at least one controller is further configured to change the first alert to a second alert based on the stimulus response and the attentiveness response.

BRIEF DESCRIPTION OF THE DRAWINGS

The embodiments of the present disclosure are pointed out with particularity in the appended claims. However, other features of the various embodiments will become more apparent and will be best understood by referring to the following detailed description in conjunction with the accompany drawings in which:

DETAILED DESCRIPTION

Figure 1:
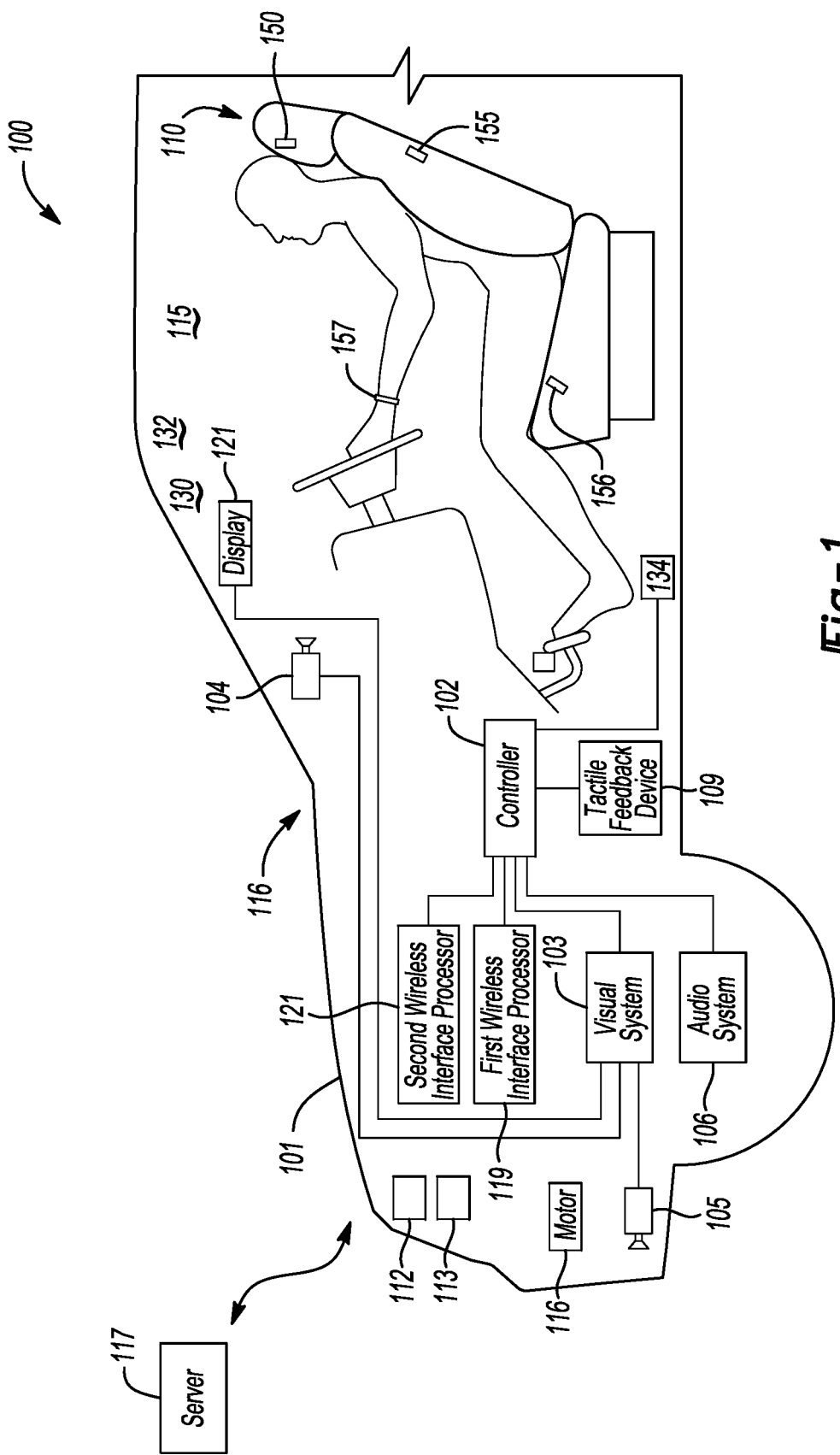
FIG. 1 depicts a system for providing biometric evoked response monitoring and feedback in accordance to one embodiment.

As required, detailed embodiments of the present invention are disclosed herein; however, it is to be understood that the disclosed embodiments are merely exemplary of the invention that may be embodied in various and alternative forms. The figures are not necessarily to scale; some features may be exaggerated or minimized to show details of particular components. Therefore, specific structural and functional details disclosed herein are not to be interpreted as limiting, but merely as a representative basis for teaching one skilled in the art to variously employ the present invention.

It is recognized that the controllers as disclosed herein may include various microprocessors, integrated circuits, memory devices (e.g., FLASH, random access memory (RAM), read only memory (ROM), electrically programmable read only memory (EPROM), electrically erasable programmable read only memory (EEPROM), or other suitable variants thereof), and software which co-act with one another to perform operation(s) disclosed herein. In addition, such controllers as disclosed utilizes one or more microprocessors to execute a computer-program that is embodied in a non-transitory computer readable medium that is programmed to perform any number of the functions as disclosed. Further, the controller(s) as provided herein includes a housing and the various number of microprocessors, integrated circuits, and memory devices ((e.g., FLASH, random access memory (RAM), read only memory (ROM), electrically programmable read only memory (EPROM), electrically erasable programmable read only memory (EEPROM)) positioned within the housing. The controller(s) as disclosed also include hardware-based inputs and outputs for receiving and transmitting data, respectively from and to other hardware-based devices as discussed herein.

Aspects disclosed herein generally provide a system and method that employs an input of a neuro monitoring device to assess occupant response to vehicle prompts that may be carried out via temporal correlation to evoked potentials for positive identification of input. Additionally, the system and method may utilize attention assessment to determine desired occupant engagement caused by the prompt.

By monitoring the neurological activity of the brain in response to audio, visual, and/or tactile inputs as well as in accordance to a cognitive attention network profile of the occupant, a biometric system can identify if the vehicle alert was registered by the user within the brain and if the desired reaction of that alert was induced. When coupled with machine learning, this may provide an intelligent human machine interface (HMI) and warning system that adapts to a user based on induced reactions or a lack thereof to personalize the alerts to improve the alert effectiveness. This aspect may allow for dynamic user prompting based upon the severity of the condition prompting the alert and the occupant's reaction to each level and type of prompt. In addition, the disclosed embodiments may provide an effective measure of the prompt against a level of drowsiness that a driver may be experiencing to successfully counteract that scenario.

FIG. 1 depicts a system 100 system for providing biometric evoked response monitoring and feedback in accordance to one embodiment. A vehicle 101 may for at least a portion of the system and includes a cabin 115 and an engine bay 116. As is generally known, the engine bay 116 houses a motor 116 that provides motive power to the vehicle 116. The system 100 includes at least one controller 102 (hereafter "the controller 102") having at least one microprocessor configured to execute any number of instructions for performing any of the disclosed operations as set forth herein. In one example, the controller 102 is configured to process sensed signals as received from any number of electrical devices in the vehicle 101. This will be discussed in more detail below. The sensed data may be stored in memory associated with the controller 102. The sensed data stored in memory associated with the controller 102 may be analyzed to determine patterns by a machine learning tool and/or artificial intelligence (AI) system that is positioned either on-board with the vehicle 101 (e.g., by the controller 102 or any other vehicle controller positioned therein) or positioned external to the vehicle 101, for example, on an external server 117.

A first wireless interface processor 119 (e.g., a vehicle to vehicle (or V2X) processor with at least one transceiver or vehicle to infrastructure (or V2I)) 104 also with at least one transceiver) is provided in the vehicle 101 for enabling wireless transmission of, but not limited to, biometric information for a driver in the vehicle 101 to the server 103. The first wireless interface processor 119 may enable bi-directional communication between the vehicle 101 and the server 117. Additionally, or alternatively, a second wireless interface processor 121 (e.g., cellular communications-based processor) may be used to establish bi-directional communication between the vehicle 101 and the server 117. The second wireless interface processor 121 may also enable WiFi connectivity in accordance to IEE802.11 and Long-Term Evolution (LTE) connectivity with the controller 102 and/or a wearable device 157 belonging to the driver of the vehicle 101.

The system 100 also includes a visual controller 103 that is operably coupled to an interior facing camera 104 and a forward-facing camera 105. A display 121 may be positioned in an instrument panel (not shown) of the cabin 115. A visual system may comprise the visual controller 103, the interior facing camera 104, the forward-facing camera 105 and the display 121. The display 121 may display images that are captured externally from the vehicle 101 via the forward-facing camera 105. The forward-facing camera 105 may capture images external from the vehicle 101 that may be indicative of possible collisions with on-coming vehicles or objects or and may also be used to detect possible lane departure incidents. The visual controller 103 may process this information and transmit to the controller 102. The controller 102 may issue a visual warning (or alert) via the display 121 to notify the driver of a possible collision or lane departure event. The interior facing camera 104 may capture the driver's response and state of attention change (or attentiveness level) in response to a stimulus (e.g., the visual alert) being provided to the driver. One example of a stimuli provided to the driver may be images captured from external to the vehicle 101 that would require the driver to take some course of action with the vehicle 101 (or mitigation step) to avoid an accident or injury. This aspect will be discussed in more detail below. The images captured by the interior facing camera 104 may be transmitted to the controller 102 via the visual controller 103 such that the controller 102 assess the driver's response and state of attentiveness as the visual alert is being provided.

The system 100 includes an audio system 106 that may include a head unit 130 (e.g., audio controller), a number of microphones 132, and a number of loudspeakers 134 positioned in the cabin 115. The audio system 106 may also sense audio in the cabin 115 and output audio into the cabin, e.g., using multiple speakers 114. The audio output from the audio system 106 may be used to alert the driver in response to a control signal from the controller 102. The audio warnings can be spoken words or tones to indicate driver distraction, change in settings, imminent danger, activation of collision warning system or combinations thereof, etc.

A tactile feedback device 109 such as, for example, a vibration device may be positioned in the cabin 115 to alert the driver in the event a warning is issued by the vehicle 101 to alert the driver of an apparent risk or injury due to a collision, driver distraction, etc. The tactile feedback device 109 may be positioned in a steering wheel or a vehicle seat 110. The tactile feedback device 109 may be a signal to vibrate a mobile electronic device associated with the vehicle and/or a passenger in the vehicle.

A laser sensing system 112, e.g., a LIDAR, is provided. The laser sensing system 112 emits light in pulses and detects the light returned after the light reflects of object external to the vehicle 100. The laser sensing system 112 may produce a digital three-dimensional representation of the external environment around the vehicle 101 in the direction of the light pulses. The laser sensing system 112 may perform laser scanning to produce a representation around the vehicle 101. The external environment may include other vehicles, signs, and other objects. The representation or individually identified objects may be provided to the controller 102 for use in the vehicle 101 as described herein. The laser sensing system 112 may communicate with the controller 102 to indicate when the vehicle 101 may encounter a possible collision with an object external to the vehicle. The controller 102 may generate an alert via the audio system 106, the tactile feedback device 109, and/or the audio system 106, and/or the tactile feedback device 109 to alert the driver.

A RADAR sensing system 113 is provided in the vehicle 101. The RADAR sensing system 113 emits radio frequency energy pulses and detects the returned pulses to identify objects around the vehicle 101 or map the external environment. The representation or individually identified objects can be provided to the controller 102 for use in the vehicle 101 as described herein. The RADAR sensing system 112 may communicate with the controller 102 to indicate when the vehicle 101 may encounter a possible collision with an object external to the vehicle. The controller 102 may generate an alert via the audio system 106, the tactile feedback device 109, and/or the audio system 106, and/or the tactile feedback device 109 to alert the driver.

The seat 110 includes a plurality of sensors 150, 155, 156 to detect various biometric characteristics of the person. The sensors 150, 155, 156 may be neurological monitors that measure electromagnetic activity of a driver's anatomy such as the driver's brain and transmit signals indicative of the driver's brain activity to the controller 102. It is recognized that the embodiments disclosed herein may also be extended to measure other anatomical features of the human body. In one example, the sensors 150, 155, 156 may by neurological monitors that are implemented as non-contact electroencephalographic (EEG) sensors which records the electromagnetic activity of the brain. In particular, the EEG sensors 150, 155, 156 may measure time-varying magnitude of electromagnetic fields that emanate from the brain. These fields may result from a collective activity of large numbers of neurons. It is recognized that the sensors 150, 155, 156 may be positioned in various pillars of the vehicle 101 (e.g., A pillars, B-pillars, C-pillars, etc.), a headliner in the vehicle cabin 115, a steering wheel, etc., as opposed to being positioned the seat 110. Further any one or more of the sensors 150, 155, and 156 may be incorporated in the wearable device 157 of the driver. In this instance, the sensors 150, 155, 156 may be configured to provide vital sign activity (e.g., body temperature, pulse rate, respiration rate, blood pressure, etc.) for the driver. The wearable device 157 may correspond to a mobile device, a smart watch, smart clothing (e.g., smart clothes or electronic textiles) that include advanced textiles interwoven with printed circuitry/sensors)), tablet, or other wireless communication device that is in the position of the driver. In this instance, the wearable device 157 may wireless communicate via the first wireless protocol controller 119 and/or the second wireless protocol controller 121 and transmit signals indicative of measured vital sign activity (e.g., body temperature, pulse rate, respiration rate, blood pressure, etc.) to the server 117. It is recognized that additional safety detection systems may be added to the vehicle 101 that detects a potential threat to the vehicle and that requires the driver to take a proactive measure with the vehicle 101 to avoid the threat in response to an alert that is generated by the vehicle 101.

In general, the controller 102 is configured to assess the driver's response when the vehicle 101 generates various alerts (e.g., audio alert with the audio system 106, visual alert with the visual system 103, and tactile alert with the tactile feedback device 109). As noted above, the alerts may be generated by any one or more of the foregoing devices to alert the driver that the vehicle 101 may be undergo a state duress (e.g., collision, accident, etc.) and the alert is generated to prompt the user to take a preventative measure to avoid the collision, accident, etc. The controller 102 is generally configured to ascertain the driver's stimulus response and state of attentiveness based on the measured electromagnetic activity of the brain based on the signals received from the EEG sensors 150, 155, 160 and/or vital sign activity from the wearable device 157 when the vehicle 101 has issued an alert. By monitoring these signals, the controller 102 may determine whether the alert was registered by the driver and if the desired reaction of that alert was induced. Overtime, the controller 102 may utilize machine learning aspects to adapt over time in the event the alerts cease to trigger the desired preventative action by the driver (e.g., various alerts become ignored over time). For example, the controller 102 may recognize that the effectiveness of the alerts may be diminishing over time based on the biometric information when the alerts are generated as the driver may enter a state habituation (e.g., a marked drop of arousal level in response to a frequently repeated stimulus).

The controller 102 may build a library of stimulus responses and attentiveness responses over time and trigger the alert that is determined to gain the most desired stimulus response and attentive state and generate such alerts in moments when the vehicle is about to enter into a state of duress. In this case, the controller 102 may (i) control the display 121 to provide a visual alert, (ii) control audio system 106 to provide an audible (or audio based alert) alert, and/or (iii) control the tactile feedback device to provide a tactile feedback device 109, and/or (iv) transmit a control signal to the wearable device to the driver to provide the alert (e.g., visual, audio, or tactile) based on the stimulus response and the attentiveness level.

Figure 2:
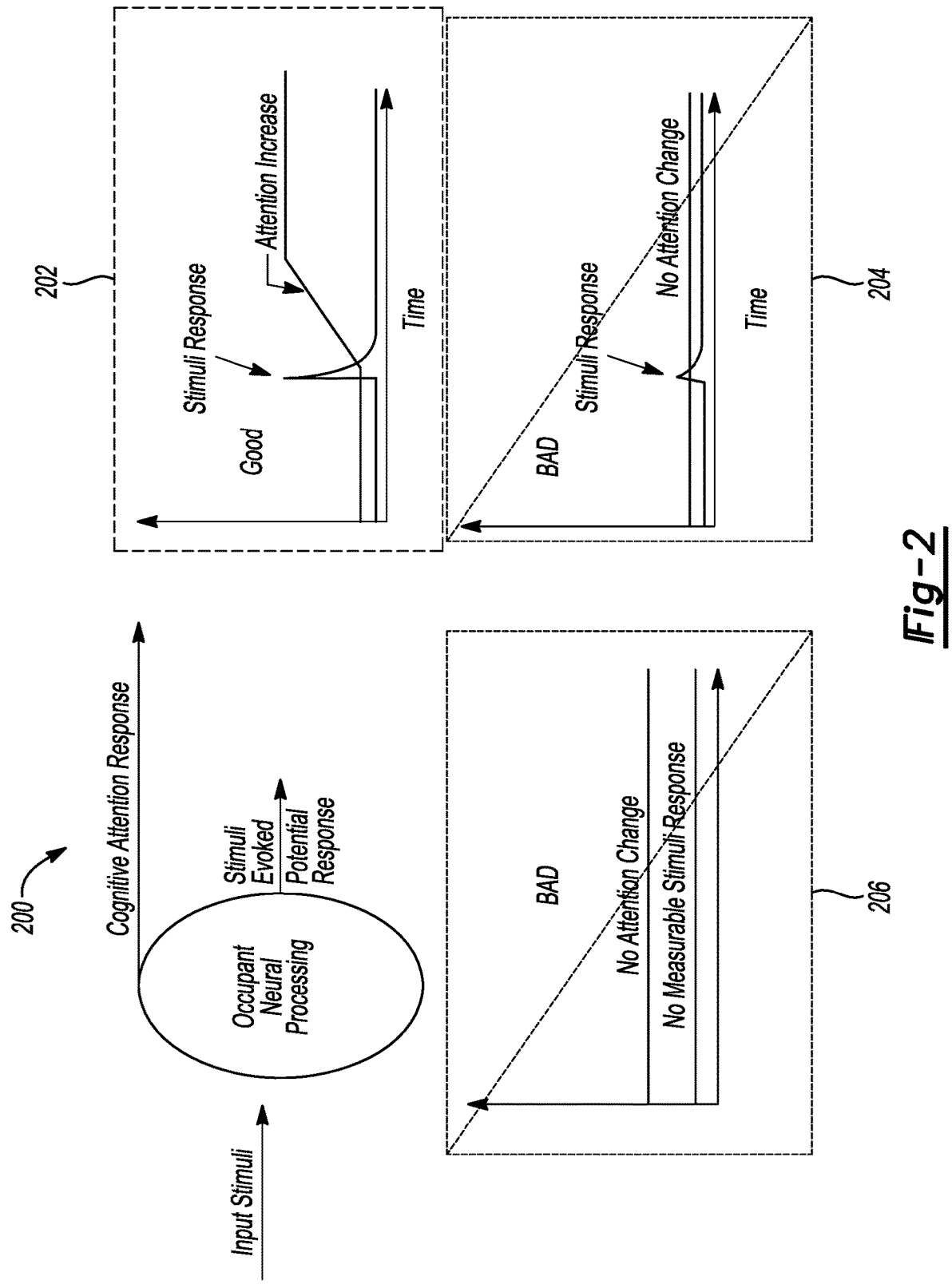
FIG. 2 is a high-level pictorial that illustrates various stimulus response and attention changes in response to an input-stimuli in accordance to one embodiment.

FIG. 2 is a high-level pictorial 200 that illustrates various stimulus response and attention (or attentiveness) changes 202, 204, 206 in response to an input-stimuli in accordance to one embodiment. At 202, the stimulus response exhibits a sharp increase and as shown the level of attention exhibits an increase over a period time and holds steady state at the increased level in response to the driver being alerted by the vehicle 101. In one non-limiting example, the period of time may correspond to an interval of 0 to 20 seconds. It is recognized that the period of time may vary based on the desired criteria of a particular implementation. In this case, the sensors 150, 155, 156 generate signals indicative of brain activity that illustrate the stimulus response and the level of attention for the driver. Additionally or alternatively, the wearable device 157 may also transmit signals indicative of vital sign activity for the driver that may also illustrate the stimulus response and the level of attention for the driver. The controller 102 determines the alert generated by the vehicle 101 is adequate to gain the driver's interest based on the stimulus response and level of attention illustrated at 202.

At 204, the stimulus response exhibits a small increase and the level of attention exhibits no change in response to the driver being alerted by the vehicle 101. The controller 102 in this case determines the alert generated by the vehicle 10 is inadequate to gain the driver's interest based on the stimulus response and level of attention illustrated at 204. At 206, the stimulus response exhibits no change and the level of attention exhibits no change in response to the driver being alerted by the vehicle 101. The controller 102 in this case determines the alert generated by the vehicle 101 is inadequate to gain the driver's interest based on the stimulus response and level of attention illustrated at 206.

Figure 3:
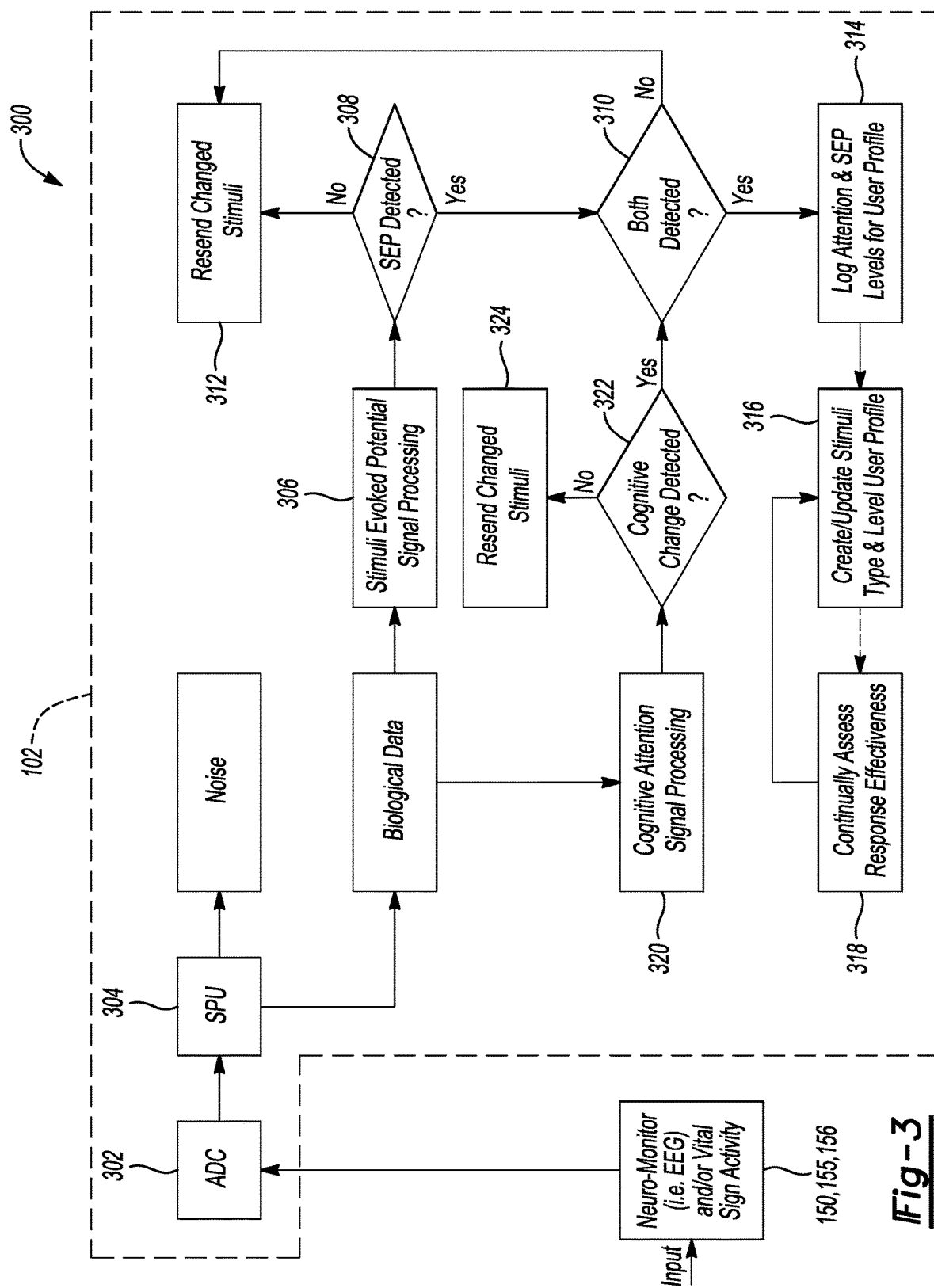
FIG. 3 depicts a functional diagram for providing biometric evoked response monitoring and feedback in accordance to one embodiment.

FIG. 3 depicts a functional diagram (or method) 300 as executed by the controller 102 for providing biometric evoked response monitoring and feedback in accordance to one embodiment. The controller 102 includes an analog to digital converter (ADC) 302 and a digital signal processor (DSP) 304. The controller 102 receives signals from the sensors 150, 155, 156 that are indicative of the driver's brain activity (e.g., EEG) and/or vital sign activity in an analog format. The ADC 302 converts the analog based sensor input into a digital signal. The DSP 304 separates the measured biological data corresponding to the brain activity and/or vital sign activity for the driver from noise that may also be part of the signal. The DSP 304 acts as a filter to remove noise from the signals received from the sensors 150, 155, 156.

At 306, the controller 102 classifies the data that corresponds to a stimuli evoked potential (SEP) of the brain activity or vital sign activity to monitor a reaction from the driver. These classifications will be used to enable the controller 102 to revise the type of alert issued over time based on changes related to the SEP over time. The SEP generally corresponds to level of the stimulus response of the driver after the vehicle 101 has issued an alert. In the case of EEG, the SEP directly relates to presence and magnitude of neurological activity of the appropriate frequency bands that indicate attentive cognitive processing. Classifying responses based upon appropriate timing, neurological manifestation and magnitude are used to categorize user-specific SEP reactivity for future use. At 308, the controller 102 looks to determine whether the SEP (or the level of the stimulus response) has exceeded a predetermined threshold. If this condition is true, then the functional diagram proceed to 310, if not, then the functional diagram 300 proceeds to 312.

At 320, the controller 102 performs cognitive attention signal processing on the signal after the ADC is performed. Additionally, the controller 102 classifies the data that corresponds to the cognitive attention level for the driver. These classifications will be used to enable the controller 102 to revise the type of alert issued over time based on changes related to the cognitive attention levels (or attentiveness levels) over time. At 322, the controller 102 determines whether the cognitive attention level of the driver has changed. If this condition is true, then the diagram 300 moves to 310. If not, then the diagram 300 moves to 324. In 310, the controller 102 determines whether both the stimulus response and the cognitive attention has changed. If this condition is true, then the diagram 300 moves to 314. If not, then the diagram 300 moves to 312.

At 314, the controller 102 stores (or logs) the level of stimulus response and attentiveness exhibited by the driver after the alert has been issued by the vehicle 101. At 316, the controller 102 creates or updates the stimulus type (e.g., visual, audible, or tactile) and the corresponding stimulus response and attentiveness level for the particular stimulus type. At 318, the controller 318 continually assess the stimulus response and level of attentiveness as stored when new data is received from the sensors 150, 155, 156 to determine if the alert is causing the driver to enter into a state of habituation. As noted above, habituation generally corresponds to a marked drop of arousal level in response to a frequently repeated stimulus.

In the event the stimulus response and/or attentiveness levels exhibited by driver start to decrease based alerts that at one point time caused increased levels of arousal for the driver, the controller 102 may generate or issue different alerts to monitor the level of arousal for the driver to ensure that the alerts generate the desired response for the driver. It is recognized that the controller 102 may use machine learning to determine the appropriate alerts to issue based on the received stimuli and attentive responses exhibited by the driver over a predetermined period of time (e.g., over a ten-hours of received data). The controller 102 may continuously monitor the levels of stimuli and attentive responses and modify/revise/adapt the issuance of alerts to coincide with positive stimulus and attentive trends exhibited by the driver over time. For example, the controller 102 may employ classification techniques to draw or infer conclusions from stored levels of stimuli responses and cognitive attentiveness. The controller 102 may then use such conclusions to generate new classifications to categorize new data regarding the stimulus response and cognitive attentive level that is received in the future. Based on the new data, the controller 102 may determine that a alert (e.g., an audio based alert) that was once able to adequately arouse the driver in response to an alert may be ineffective and that a different alert (e.g., tactile based alert) may be required to arose the driver to take a corrective action in response to the alert.

It is recognized that all of the functions performed by the controller 102 with respect to determining the stimulus response and attentiveness response as noted in connection with FIG. 3 may also be performed at the server 117. In this instance, the vehicle 101 may transmit via the first wireless interface processor 119 and/or the second wireless interface processor 121 the signals received from the sensors 150, 155, 156 including the wearable device 157 to the server 117 for processing and the determination in terms of which alert (e.g., tactile, audio, or visual) achieves the most favorable result in terms of obtaining the driver's attention when the alert is triggered. The server 117 may wirelessly transmit the desired alert to be provided to the driver in moments in which the vehicle 101 is required to provide an alert to notify the driver (e.g., this information may be transmitted to the controller 102 of the vehicle 101).

While exemplary embodiments are described above, it is not intended that these embodiments describe all possible forms of the invention. Rather, the words used in the specification are words of description rather than limitation, and it is understood that various changes may be made without departing from the spirit and scope of the invention. Additionally, the features of various implementing embodiments may be combined to form further embodiments of the invention.

What is claimed is:

1. A system for performing biometric evoked response monitoring and feedback for a vehicle, the system comprising:

a plurality of sensors for being positioned about a main cabin of the vehicle and each sensor being configured to provide a first signal indicative of a measured electromagnetic characteristic of an anatomical feature of a driver for the vehicle in response to an alert being issued to the driver; and at least one controller being configured to:
receive the first signal;
determine a stimulus response and an attentiveness response of the driver based on the measured electromagnetic characteristic of the anatomical feature of the driver,
wherein the stimulus response corresponds to a stimuli evoked potential (SEP) of brain activity or vital sign activity for the driver,
wherein the at least one controller is further configured to:
compare a level of the SEP to a predetermined threshold; and
store the SEP for a user profile in memory in response to at least the level of the SEP exceeding the predetermined threshold, and
wherein the at least one controller is further configured to receive a second signal indicative of the measured electromagnetic characteristic of the anatomical feature of the driver of the vehicle from a wearable device on the driver in response to the vehicle transmitting the alert to the driver.

2. The system of claim 1, wherein the at least one controller is further configured to control a visual system to provide a visual alert for the driver based on the stimulus response and the attentiveness response.

3. The system of claim 1, wherein the at least one controller is further configured to control an audio system to provide an audio-based alert for the driver based on the stimulus response and the attentiveness response.

4. The system of claim 1, wherein the at least one controller is further configured to control a tactile feedback device to provide a tactile based alert for the driver based on the stimulus response and the attentiveness response.

5. The system of claim 1, wherein the plurality of sensors comprise a plurality of electroencephalographic (EEG) sensors and the anatomical feature of the driver is a brain of the driver.

6. The system of claim 1, wherein the at least one controller is further configured to provide a desired alert that arouses the driver to perform a mitigating action based on both the stimulus response and the attentiveness response exhibiting an increase over time.

7. The system of claim 1, wherein the at least one controller is further configured to classify a plurality of stimulus responses and attentiveness responses for the driver over a predetermined amount of time in response to a plurality of different alerts being generated in the vehicle.

8. The system of claim 1, wherein the at least one controller is further configured change the alert to a different alert in response to determining that the driver has entered a state of habituation based on receiving a plurality of stimulus responses and attentiveness responses for the driver over a predetermined amount of time.

9. The system of claim 1, wherein the at least one controller is further configured to transmit a control signal to the wearable device to generate the alert based on the stimulus response and the attentiveness response of the driver.

10. A system for performing biometric evoked response monitoring and feedback for a vehicle, the system comprising:
   a plurality of sensors for being positioned about a main cabin of the vehicle and each sensor being configured to provide a first signal indicative of a measured electromagnetic characteristic of an anatomical feature of a driver of the vehicle in response to a first alert being issued to the driver; and
   at least one controller being configured to:
      receive the first signal;
      determine a stimulus response and an attentiveness response of the driver based on the measured electromagnetic characteristic of the anatomical feature of the driver; and
      change the first alert to a second alert based on the stimulus response and the attentiveness response,
   wherein the stimulus response corresponds to a stimuli evoked potential (SEP) of brain activity or vital sign activity for the driver and,
   wherein the at least one controller is further configured to:
      compare a level of the SEP to a predetermined threshold; and
      store the SEP for a user profile in memory in response to at least the level of the SEP exceeding the predetermined threshold, and
   wherein the at least one controller is further configured change the second alert to a different alert in response to determining that the driver has entered a state of habituation based on receiving a plurality of stimulus responses and attentiveness responses over a predetermined amount of time.

11. The system of claim 10, wherein the at least one controller is further configured to change the first alert to the second alert based on both the stimulus response and the attentiveness response exhibiting an increase over time.

12. The system of claim 10, wherein the at least one controller is further configured to classify a plurality of a stimulus responses and attentiveness responses over a predetermined amount of time in response to the first alert being issued to the driver.

13. A system for performing biometric evoked response monitoring and feedback for a vehicle, the system comprising:
   a plurality of electroencephalographic (EEG) sensors for being positioned in a vehicle, each EEG sensor being configured to provide a first signal indicative of a measured electromagnetic characteristic of an anatomical feature of a driver of the vehicle in response to the vehicle transmitting a first alert to the driver; and
   at least one controller being configured to:
      receive the first signal;
      determine a stimulus response and an attentiveness response of the driver based on the measured electromagnetic characteristic of the anatomical feature of the driver; and
      change the first alert to a second alert based on the stimulus response and the attentiveness response,
   wherein the stimulus response corresponds to a stimuli evoked potential (SEP) of brain activity or vital sign activity for the driver, and
   wherein the at least one controller is further configured to:
      compare a level of the SEP to a predetermined threshold; and
      store the SEP for a user profile in memory in response to at least the level of the SEP exceeding the predetermined threshold, and
   wherein the at least one controller is further configured to receive a second signal indicative of a measured vital sign characteristic of the anatomical feature of the driver of the vehicle from a wearable device on the driver in response to the vehicle transmitting the first alert to the driver.

14. The system of claim 13, wherein the at least one controller is further configured change the second alert to a different alert in response to determining that the driver has entered a state of habituation based on receiving a plurality of stimulus responses and attentiveness responses over a predetermined amount of time.

15. The system of claim 1, wherein the attentiveness response of the driver corresponds to a cognitive attention level for the driver, and wherein the at least one controller is further configured to determine whether the cognitive attention level for the driver has changed over time and to store the SEP and the cognitive attention level for the user profile in the memory in response to the level of the SEP exceeding the predetermined threshold and the cognitive attention level for the driver changing over time.

16. The system of claim 10, wherein the attentiveness response of the driver corresponds to a cognitive attention level for the driver, and wherein the at one least controller is further configured to determine whether the cognitive attention level for the driver has changed over time and to store the SEP and the cognitive attention level for the user profile in the memory in response to the level of the SEP exceeding the predetermined threshold and the cognitive attention level for the driver changing over time.

17. The system of claim 13, wherein the attentiveness response of the driver corresponds to a cognitive attention level for the driver, and wherein the at one least controller is further configured to determine whether the cognitive attention level for the driver has changed over time and to store the SEP and the cognitive attention level for the user profile in the memory in response to the level of the SEP exceeding the predetermined threshold and the cognitive attention level for the driver changing over time.

* * * * *